US 11,828,824 B2

(12) United States Patent
Zhu et al.

(10) Patent No.: US 11,828,824 B2
(45) Date of Patent: Nov. 28, 2023

(54) SYSTEM AND METHOD FOR DEEP LEARNING-BASED ACCELERATED MAGNETIC RESONANCE IMAGING WITH EXTENDED FIELD OF VIEW COIL SENSITIVITY CALIBRATION

(71) Applicant: GE PRECISION HEALTHCARE LLC, Wauwatosa, WI (US)

(72) Inventors: Xucheng Zhu, Mountain View, CA (US); Graeme Colin McKinnon, Hartland, WI (US); Andrew James Coristine, Senneville (CA); Martin Andreas Janich, Munich (DE)

(73) Assignee: GE Precision Healthcare LLC, Wauwatosa, WI (US)

( * ) Notice: Subject to any disclaimer, the term of this patent is extended or adjusted under 35 U.S.C. 154(b) by 498 days.

(21) Appl. No.: 17/204,531

(22) Filed: Mar. 17, 2021

(65) Prior Publication Data
US 2022/0299588 A1    Sep. 22, 2022

(51) Int. Cl.
*G01R 33/561* (2006.01)
*G01R 33/48* (2006.01)
(Continued)

(52) U.S. Cl.
CPC ...... *G01R 33/5611* (2013.01); *G01R 33/4818* (2013.01); *G01R 33/58* (2013.01);
(Continued)

(58) Field of Classification Search
CPC ............ G01R 33/5611; G01R 33/4818; G01R 33/58; G16H 30/40; G06N 3/02; G06N 3/0464; G06T 11/003; G06T 11/005
See application file for complete search history.

(56) References Cited

U.S. PATENT DOCUMENTS 10,671,939 B2    6/2020 Knoll et al.
10,712,416 B1    7/2020 Sandino et al.
(Continued)

OTHER PUBLICATIONS

Hammernik, Kerstin, et al.; "Learning a Variational Network for Reconstruction of Accelerated MRI Data", Magnetic Resonance in Medicine, Jun. 2018; 79(6): 3055-3071. (Published online 2017 doi: 10.1002/mrm.26977); pp. 1-29.
(Continued)

*Primary Examiner* — Utpal D Shah
(74) *Attorney, Agent, or Firm* — Fletcher Yoder P.C.

(57) ABSTRACT

Image reconstruction systems and methods include providing sensitivity maps for coils of a magnetic resonance imaging (MRI) system to a neural network. The systems and methods also include providing interleaved k-space data to the neural network, wherein the interleaved k-space data includes partial k-space data interleaved with zeros, or synthesized k-space data, to provide an extended field of view (FOV) different from a FOV utilized during acquisition of the partial k-space data, wherein the partial k-space data were obtained during a scan of a region of interest with the MRI system. The systems and methods further include outputting, from the neural network, a final reconstructed MR image based at least on the sensitivity maps and the interleaved k-space data, wherein the final reconstructed MR image includes the FOV utilized during the acquisition of the partial k-space data.

20 Claims, 4 Drawing Sheets

(51) Int. Cl.
   *G06N 3/02*      (2006.01)
   *G06N 3/0464*    (2023.01)
   *G06T 11/00*     (2006.01)
   *G16H 30/40*     (2018.01)
   *G01R 33/58*     (2006.01)

(52) U.S. Cl.
   CPC ............. *G06N 3/02* (2013.01); *G06N 3/0464* (2023.01); *G06T 11/003* (2013.01); *G06T 11/005* (2013.01); *G16H 30/40* (2018.01)

(56) References Cited

U.S. PATENT DOCUMENTS

2011/0148410 A1* 6/2011 Zaitsev .............. G01R 33/5611
                                                    324/309
2019/0041481 A1* 2/2019 Subbarao ........... G01R 33/3415
2023/0186532 A1* 6/2023 Schuelke .............. G06N 3/084
                                                    324/309

OTHER PUBLICATIONS

Sandino, Christopher M., et al.; "Accelerating Cardiac Cine MRI Using a Deep Learning-Based ESPIRiT Reconstruction", Magnetic Resonance in Medicine, Jun. 2020 doi: 10.1002/mrm.28420; pp. 1-16.

* cited by examiner

SYSTEM AND METHOD FOR DEEP LEARNING-BASED ACCELERATED MAGNETIC RESONANCE IMAGING WITH EXTENDED FIELD OF VIEW COIL SENSITIVITY CALIBRATION

BACKGROUND

The subject matter disclosed herein relates to medical imaging and, more particularly, to systems and methods for deep learning-based accelerated magnetic resonance imaging (MRI) with extended field of view coil sensitivity calibration.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

Recently, deep learning (DL)-based reconstruction approaches have been utilized in MRI to accelerate MR scans by leveraging the learned prior information from historical MRI data. Most of the deep learning-based reconstruction frameworks incorporate parallel imaging technique (which requires sensitivity information of multi-channel coils array) to further increase the acceleration factor. Self-calibration is a widely used coil sensitivity calibration strategy (e.g., C3 calibration) that utilizes fully sampled center k-space to estimate sensitivity maps. However, scans with a limited field of view (FOV) may cause problematic sensitivity estimation leading to degradation of the final reconstructed image. In particular, when MR scans are acquired in a limited FOV, in the phase encoding direction, tissue wrapping effects (aliasing) may be amplified with iterative DL reconstruction resulting in degraded final reconstructed images. In addition, certain reconstruction approaches may increase computation time. Therefore, there is a need for an alternative approach to provide sensitivity information.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a DL-based image reconstruction system is provided. The system includes a memory encoding processor-executable routines. The system also includes a processing component configured to access the memory and to execute the processor-executable routines, wherein the routines, when executed by the processing component, cause the processing component to perform actions. The actions include providing sensitivity maps for coils of a magnetic resonance imaging (MRI) system to a neural network. The actions also include providing interleaved k-space data to the neural network, wherein the interleaved k-space data includes partial k-space data interleaved with zeros, or synthesized k-space data, to provide an extended field of view (FOV) different from a FOV utilized during acquisition of the partial k-space data, wherein the partial k-space data were obtained during a scan of a region of interest with the MRI system. The actions further include outputting, from the neural network, at least one final reconstructed MR image based at least on the sensitivity maps and the interleaved k-space data, wherein the at least one final reconstructed MR image includes the FOV utilized during the acquisition of the partial k-space data.

In another embodiment, a deep learning-based image reconstruction method is provided. The method includes providing, via a processor, sensitivity maps for coils of a magnetic resonance imaging (MRI) system to a neural network. The method also includes providing, via the processor, interleaved k-space data to the neural network, wherein the interleaved k-space data includes partial k-space data interleaved with zeros, or synthesized k-space data, to provide an extended field of view (FOV) different from a FOV utilized during acquisition of the partial k-space data, wherein the partial k-space data were obtained during a scan of a region of interest with the MRI system. The method further includes outputting from the neural network, via the processor, at least one final reconstructed MR image based at least on the sensitivity maps and the interleaved k-space data, wherein the at least one final reconstructed MR image includes the FOV utilized during the acquisition of the partial k-space data.

In a further embodiment, a non-transitory computer-readable medium, the computer-readable medium including processor-executable code that when executed by a processor, causes the processor to perform actions. The actions include providing sensitivity maps for coils of a magnetic resonance imaging (MRI) system to a neural network. The actions also include providing interleaved k-space data to the neural network, wherein the interleaved k-space data includes partial k-space data interleaved with zeros, or synthesized k-space data, to provide an extended field of view (FOV) different from a FOV utilized during acquisition of the partial k-space data, wherein the partial k-space data were obtained during a scan of a region of interest with the MRI system. The actions further include outputting, from the neural network, at least one final reconstructed MR image based at least on the sensitivity maps and the interleaved k-space data, wherein the at least one final reconstructed MR image includes the FOV utilized during the acquisition of the partial k-space data.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

Deep-learning (DL) approaches discussed herein may be based on artificial neural networks, and may therefore encompass one or more of deep neural networks, fully connected networks, convolutional neural networks (CNNs), unrolled neural networks, perceptrons, encoders-decoders, recurrent networks, wavelet filter banks, u-nets, general adversarial networks (GANs), or other neural network architectures. The neural networks may include shortcuts, activations, batch-normalization layers, and/or other features. These techniques are referred to herein as DL techniques, though this terminology may also be used specifically in reference to the use of deep neural networks, which is a neural network having a plurality of layers.

As discussed herein, DL techniques (which may also be known as deep machine learning, hierarchical learning, or deep structured learning) are a branch of machine learning techniques that employ mathematical representations of data and artificial neural networks for learning and processing such representations. By way of example, DL approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

The present disclosure provides systems and methods for improving DL-based accelerated MRI reconstruction. In particular, external coil sensitivity calibration is utilized to improve image reconstruction. Specifically, an extended FOV calibration MRI acquisition (e.g., with a first FOV large enough to cover an imaged object of interest) is performed from which coil sensitivity maps are extracted, while in a separate acquisition (e.g., with a second FOV smaller than the first FOV) of an object of interest (e.g., accelerated MRI scan utilizing parallel imaging techniques) partial or undersampled k-space data are obtained. The extended FOV calibration MRI acquisition and the acquisition of the data utilizing the smaller FOV may occur in the same imaging scan or in separate imaging scans. In a separate scan, the extended FOV calibration scan is considered an external calibration MRI scan. The partial k-space data are interleaved with zeros, or synthesized k-space data, to extend the FOV (e.g., in a phase encoding dimension). The interleaved k-space data with the extended FOV and the coil sensitivity maps are inputted into a neural network (e.g., unrolled neural network) that performs image reconstruction and outputs one or more final reconstructed images. The neural network may generate one or more reconstructed images from the interleaved k-space data with the extended FOV and the coil sensitivity maps and adjust the FOV of the reconstructed images (to the FOV utilized during acquisition of the partial k-space data) to generate the final reconstructed images. The improved DL-based accelerated MRI reconstruction utilizing external coil sensitivity calibration may minimize or eliminate aliasing artifacts (i.e., tissue wrapping effects) that typically occur with iterative DL reconstruction while maintaining image quality.

Figure 1:
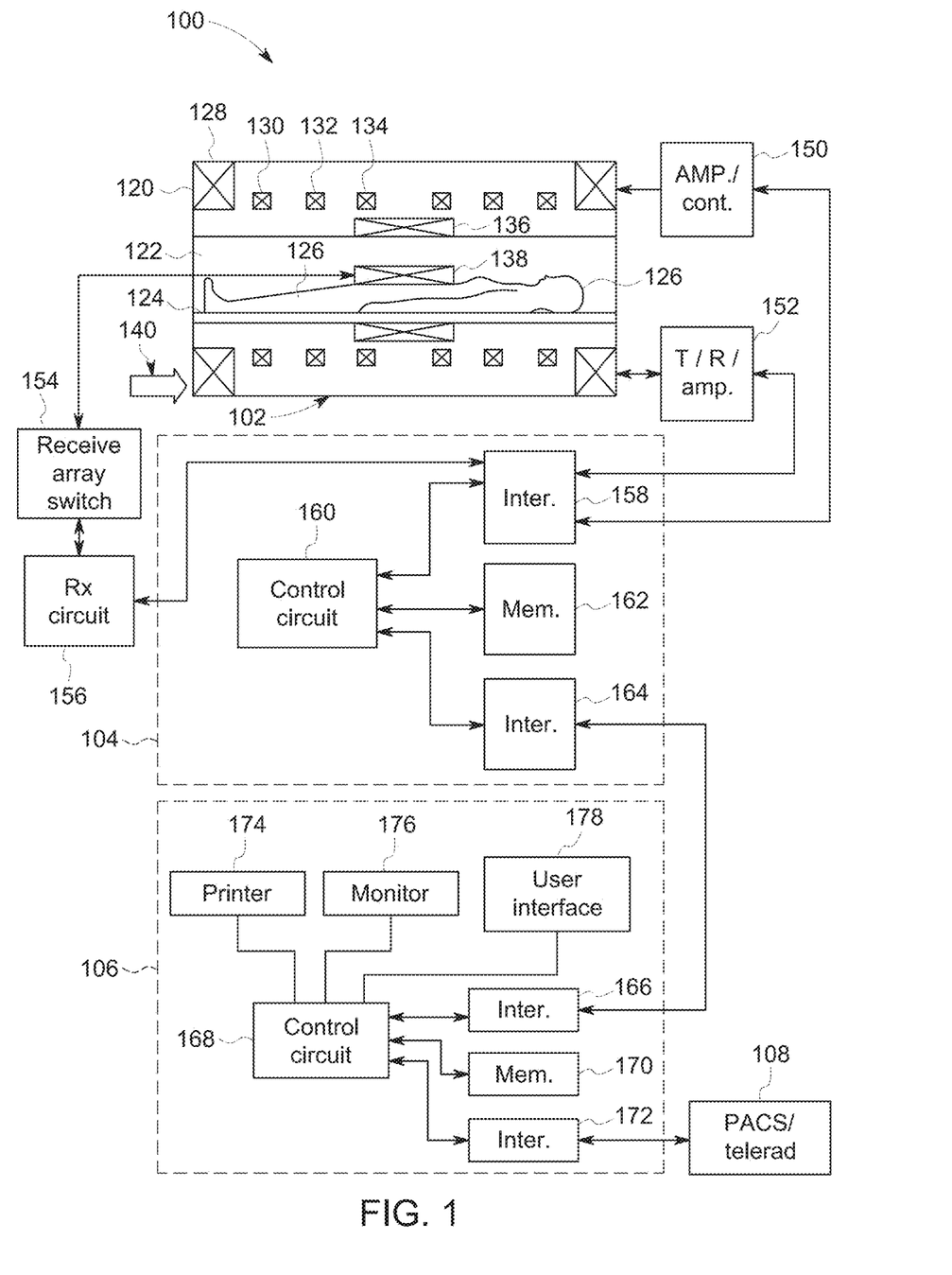
FIG. 1 illustrates an embodiment of a magnetic resonance imaging (MRI) system suitable for use with the disclosed technique.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 to be positioned therein for imaging selected anatomy within the patient.

Scanner 102 includes a series of associated coils for producing controlled magnetic fields for exciting the gyromagnetic material within the anatomy of the subject being imaged. Specifically, a primary magnet coil 128 is provided for generating a primary magnetic field, BO, which is generally aligned with the bore 122. A series of gradient coils 130, 132, and 134 permit controlled magnetic gradient fields to be generated for positional encoding of certain of the gyromagnetic nuclei within the patient 126 during examination sequences. A radio frequency (RF) coil 136 is configured to generate radio frequency pulses for exciting the certain gyromagnetic nuclei within the patient. In addition to the coils that may be local to the scanner 102, the system 100 also includes a set of receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain of the gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, Bo. A power input 44 (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuit 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuit 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuit 104 and system control circuit 106. In certain embodiments, the control and analysis circuit 160, while illustrated as a single unit, may include one or more hardware devices. The system control circuit 106 includes an interface circuit 166, which receives data from the scanner control circuit 104 and transmits data and commands back to the scanner control circuit 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data as described below. In certain embodiments, the memory circuit 170 may store one or more neural networks for reconstruction of acquired data as described below. In certain embodiments, image reconstruction may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
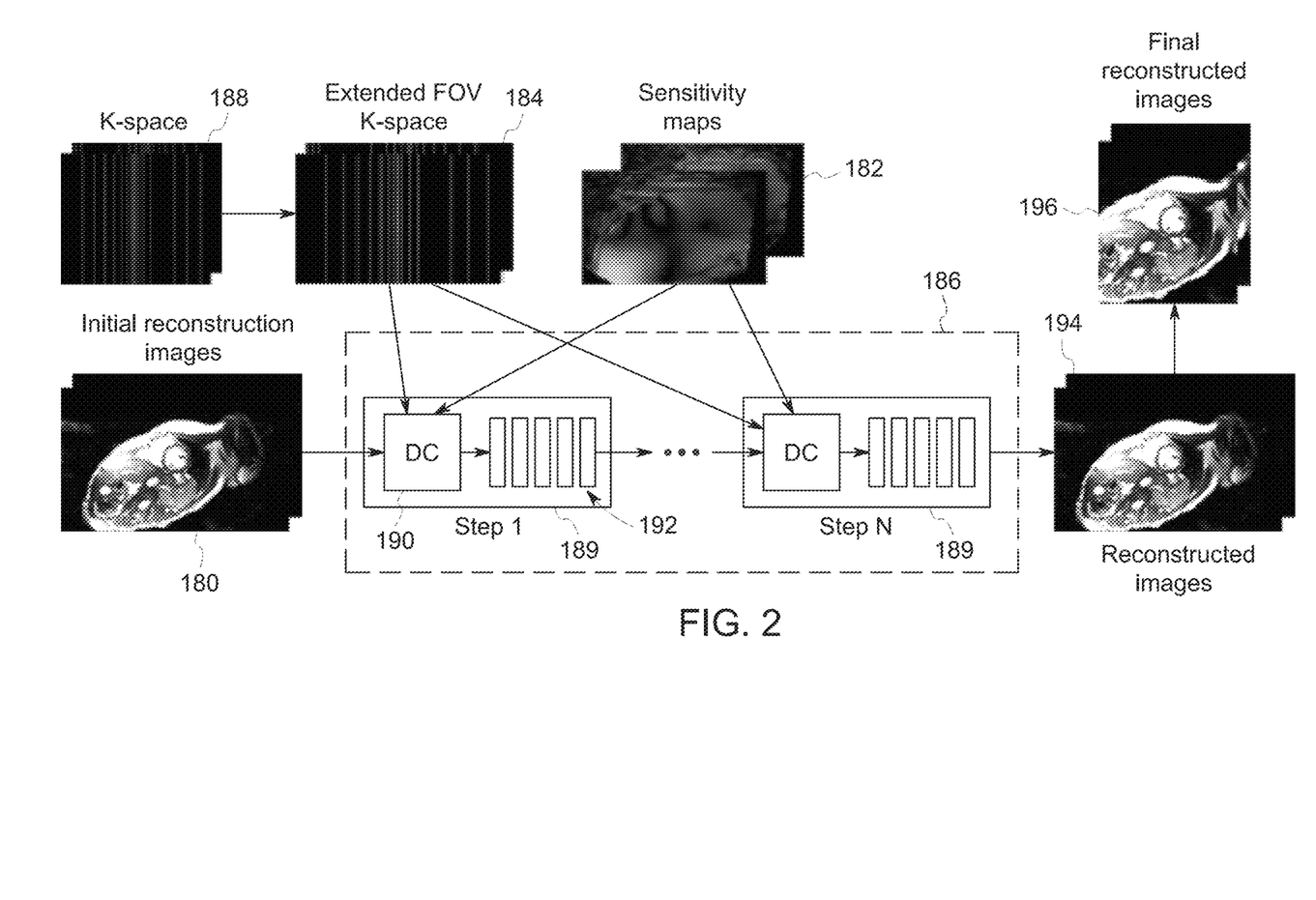
FIG. 2 is a schematic diagram illustrating utilization of a neural network for DL-based MRI reconstruction with extended FOV coil sensitivity calibration, in accordance with aspects of the present disclosure.

FIG. 2 is a schematic diagram illustrating utilization of a neural network for DL-based MRI reconstruction with extended FOV coil sensitivity calibration (external coil sensitivity calibration when calibration data is acquired in a separate scan). The DL-based MRI reconstruction with FOV coil sensitivity calibration may be carried out on the circuitry of the MRI system 100 in FIG. 1 or on a separate computing device. As an alternative to typical self-calibration methods, an extended FOV calibration scan may be utilized to obtain coil sensitivity (in separate scans or the same scan). Unlike typical self-calibration, an extended FOV calibration acquisition may have a different prescribed FOV from a target sequence (i.e., acquisition scan to obtain image data for object of interest). Therefore, the calibration scan would have a large FOV to cover the image subject and avoid the aliasing effect in sensitivity calibration. In addition, external calibration scan parameters are optimized to maximize image signal-to-noise ratio while minimizing other image artifact effects (e.g., chemical shift). Further, a scan time for an external calibration scan may take less than 10 seconds and, thus, would not significantly prolong the whole MR scan.

As depicted in FIG. 2, the extended FOV calibrated coil sensitivity may be utilized in combination with a neural network-based (e.g., unrolled neural network) reconstruction. As depicted, one or more initial images (MR images) 180, coil sensitivity maps 182, and extended FOV k-space data 184 are fed as inputs to a DL image reconstruction network 186 (e.g., neural network).

Prospective undersampled or partial k-space data 188 (e.g., multi-phase k-space data) were acquired from an MRI scan of an object of interest (e.g., a portion of a patient) at a first FOV. In certain embodiments, the k-space data may be acquired during a Cine imaging sequence to capture motion (e.g., of the heart during different phased of the cardiac cycle). In certain embodiments, the MRI scan is an accelerated scan utilizing parallel imaging technique (e.g., where signals from individual coils are amplified, digitized, and processed simultaneously along separate channels) to reduce scan time. The extended FOV k-space data 184 were derived from interleaving the undersampled k-space data 188 with zeros (e.g. in the phase encoding dimension), or synthesized k-space data, to extend the FOV so that it is different from (and larger than) the FOV utilized during the scan to acquire the undersampled k-space data 188. The one or more initial images 180 are reconstructed by coil-combined reconstruction of the extended FOV k-space data 184.

The coil sensitivity maps 182 are extracted from the data acquired during an external calibration scan (at a second FOV) that is separate from accelerated scan of the object of interest. For example, the external calibration scan may occur prior to or subsequent to the accelerated scan. In certain embodiments, the coil sensitivity maps 182 are extracted from calibration data (at the second FOV) acquired during the same scan. The second FOV is different from (and larger than) the first FOV (utilized during the acquisition of the k-space data). The coil sensitivity maps 182 are extracted from the calibration data according to both the location of the target scan (e.g., accelerated scan) and the extended FOV of the extended FOV k-space data 184. The coil sensitivity maps 182 include a calibration FOV that matches the extended FOV. Area outside a central k-space region of the calibration FOV is filled with zeros for all channels.

As depicted, the DL image reconstruction network 186 is an unrolled neural network. In particular, in accordance with certain aspects the image reconstruction is represented as an unrolled (i.e. non-looped) process, in which all the computation steps occur in a fixed sequence without repetitions, and in which the data fidelity computation and/or the image update computation incorporate a neural network. Due to the unrolled nature of the iterated steps, different neural networks or models may be employed at different stages or steps of the process so as to optimize the performance of the reconstruction process. Alternatively, the same neural network or model may be used at multiple (or all) repeated steps (e.g., data-fit steps and/or image update steps) of the unrolled process. In contrast, an iterated process that is not unrolled (i.e., is looped) repeats the same operation each iteration. The network 186 may be trained with retrospectively undersampling thousands of fully sampled images. The fully sampled images may be utilized as ground truths. In certain embodiments, a different type of neural network may be utilized by the network 186.

The DL image reconstruction network 186 includes a number of steps or iterative blocks 189 (e.g., as depicted Step 1 to Step N). The number of steps 189 may vary. The steps 189 are connected by direct connections from one step to the following step. Each step or iterative block 189 includes a data consistency layer or unit 190 and an image domain neural network layer or regularization unit 192. The data consistency layers 190 are configured to preserve fidelity of the coil data in the respective step or iterative block outputs. The image domain neural network layers 192 are configured to generate regularization information based on the respective outputs from the respective proceeding iterative blocks or steps. The regularization information is representative of additional information required to reduce generalization error in output of each of the iterative blocks or steps.

The image domain neural network layers 192 may be formed of a fully convolutional residual network (e.g., 3D spatiotemporal convolutional neural network). Each image domain neural network 192 may consist of multiple 3D convolutional layers (e.g., each having 3×3×3 kernels) that are utilized using circular padding along the phase encoding and temporal directions to enforce circular boundary conditions in the two dimensions. The initial convolution expands the one or more images into feature maps that are propagated through the network until the final convolution where the feature maps are recombined into the original number of input images. Each convolutional layer is preceded by ReLU pre-activation layers that operate separately on each image/feature channel.

As depicted, the one or more initial images 180, the coil sensitivity maps 182, and the extended FOV k-space data 184 are fed into the data consistency layer 190 of Step 1 which is coupled to and provides one or more input images to the image domain neural network layer 192 via a single image channel. In certain embodiments, the data consistency layer 190 and the image domain neural network layer 192 are coupled via multiple image channels. One or more output images generated by the image domain neural network layer 192 and provided to the data consistency layer 190 of the next step or iterative block 189 (along with the coil sensitivity maps 182 and the extended FOV k-space data 184). This process occurs at each subsequent step. The final step 189 or iterative block (i.e., Step N) outputs one or more reconstructed images 194. The FOV of the one or more reconstructed images 194 (which are at the extended FOV) are altered to the FOV utilized during the acquisition of the undersampled k-space data 188 to generate one or more final reconstructed images 196 (MR images). Each reconstructed image 194 generated by the network 186 is a multi-channel output which is combined into a single channel in the final reconstructed image 196. The final reconstructed images 196 are free of aliasing artifacts.

Figure 3:
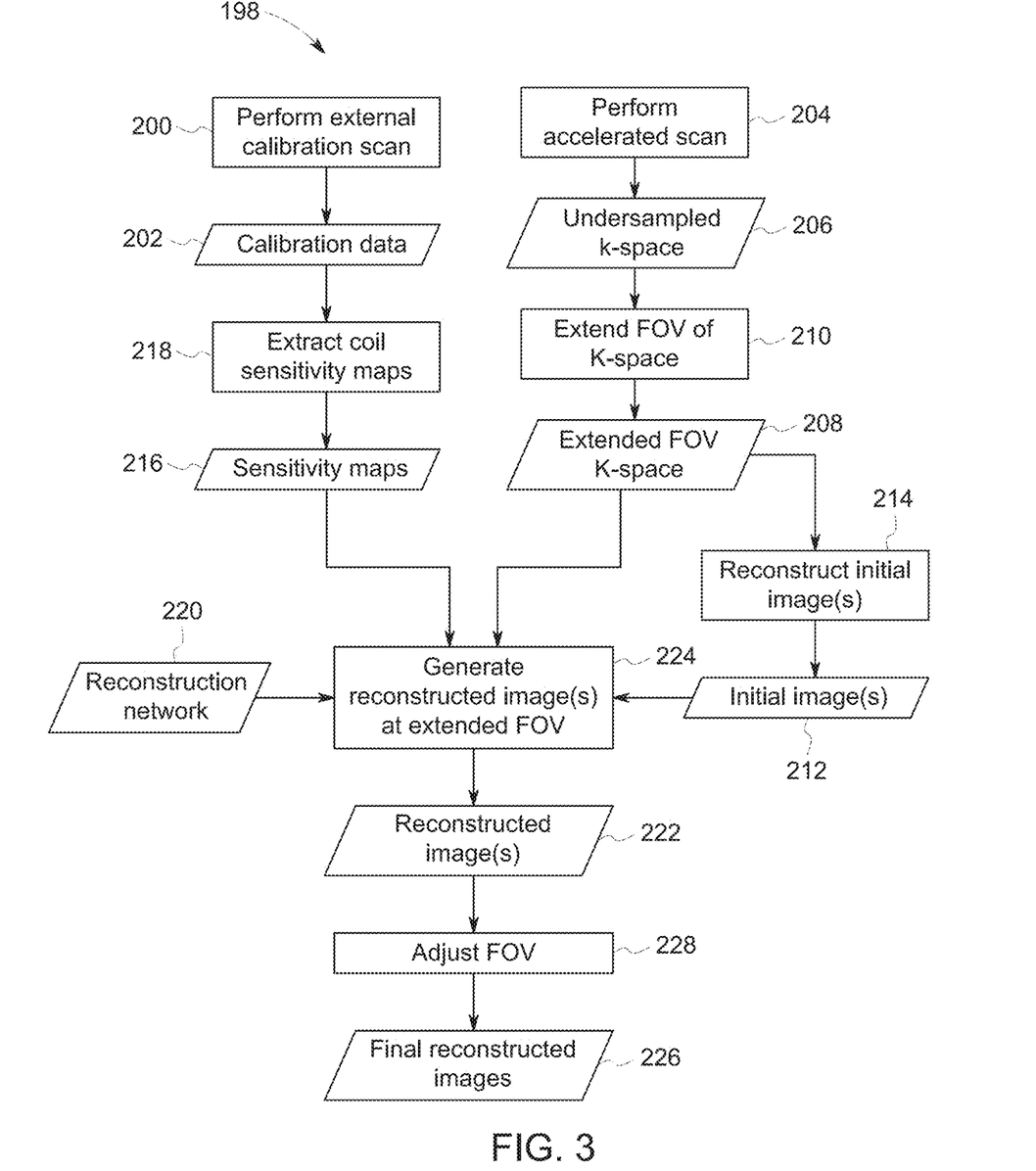
FIG. 3 is a flow chart of a method for DL-based MRI reconstruction with external coil sensitivity calibration, in accordance with aspects of the present disclosure.

FIG. 3 is a flow chart of a method 198 for DL-based MRI reconstruction with external coil sensitivity calibration. One or more components of the MRI system 100 in FIG. 1 may be utilized for performing the method 198. One or more steps of the method 198 may be performed simultaneously or in a different order from that depicted in FIG. 3. The method 198 includes performing a separate external calibration scan with an MRI system (block 200) to obtain calibration data 202. The method 198 also include performing an accelerated scan (e.g., utilizing parallel imaging technique) with the MRI system (block 204) on an object of interest (e.g., portion of a body of a patient) to obtain partial or undersampled k-space data (e.g., multi-phase k-space data). The separate external calibration scan may occur prior to or subsequent to the accelerated scan. In certain embodiments, the external calibration scan and the accelerated scan may utilize different acquisition sequences. For example, the external calibration scan may utilize a 3D GRE based coil calibration sequence and the accelerated scan may utilize a 2D accelerated Cine sequence or a balanced steady-state gradient echo sequence. In certain embodiments, the calibration data may be acquired during the same scan. In either case, the FOV utilized to acquire the calibration data is larger than the FOV utilized during the accelerated portion of the scan.

The method 198 includes extending the FOV of the undersampled k-space data 206 to generate extended FOV k-space data 208 (block 210). The extended FOV k-space data 208 are formed by interleaving the undersampled k-space data 206 with zeros, or synthesized k-space data. The extended FOV of the extended FOV k-space data 208 is larger than the FOV utilized to acquire the undersampled k-space but smaller than the FOV of the calibration scan. The method 198 also includes reconstructing one or more initial images 214 from the undersampled k-space data 206 (block 212).

The method 198 further includes extracting coil sensitivity maps 216 from the calibration data 202 (block 218). The coil sensitivity maps 216 are extracted from the external calibration data 202 according to both the location of the target scan (e.g., accelerated scan) and the extended FOV of the extended FOV k-space data 208. In certain embodiments, the coil sensitivity maps are extracted from calibration data acquired during the target scan. The coil sensitivity maps 216 include an external calibration FOV that matches the extended FOV. Area outside a central k-space region of the calibration FOV is filled with zeros for all channels.

The method 198 even further includes providing the sensitivity maps 216, the extended FOV k-space data 208, and the one or more initial images 212 to a reconstruction network 220 (e.g., unrolled neural network) that generates one or more reconstructed images 222 based on the sensitivity maps 216, the extended FOV k-space data 208, and the one or more initial images 212 (block 224). The reconstruction network 220 is as described in FIG. 2. The reconstructed images 222 have the extended FOV. The method 198 still further includes adjusting the FOV of the reconstructed images 222 to generate final reconstructed images 226 (block 228). The final reconstructed images 226 have the FOV utilized in the acquisition of the undersampled k-space data 206. The final reconstructed images 226 are free of aliasing artifacts.

Figure 4:
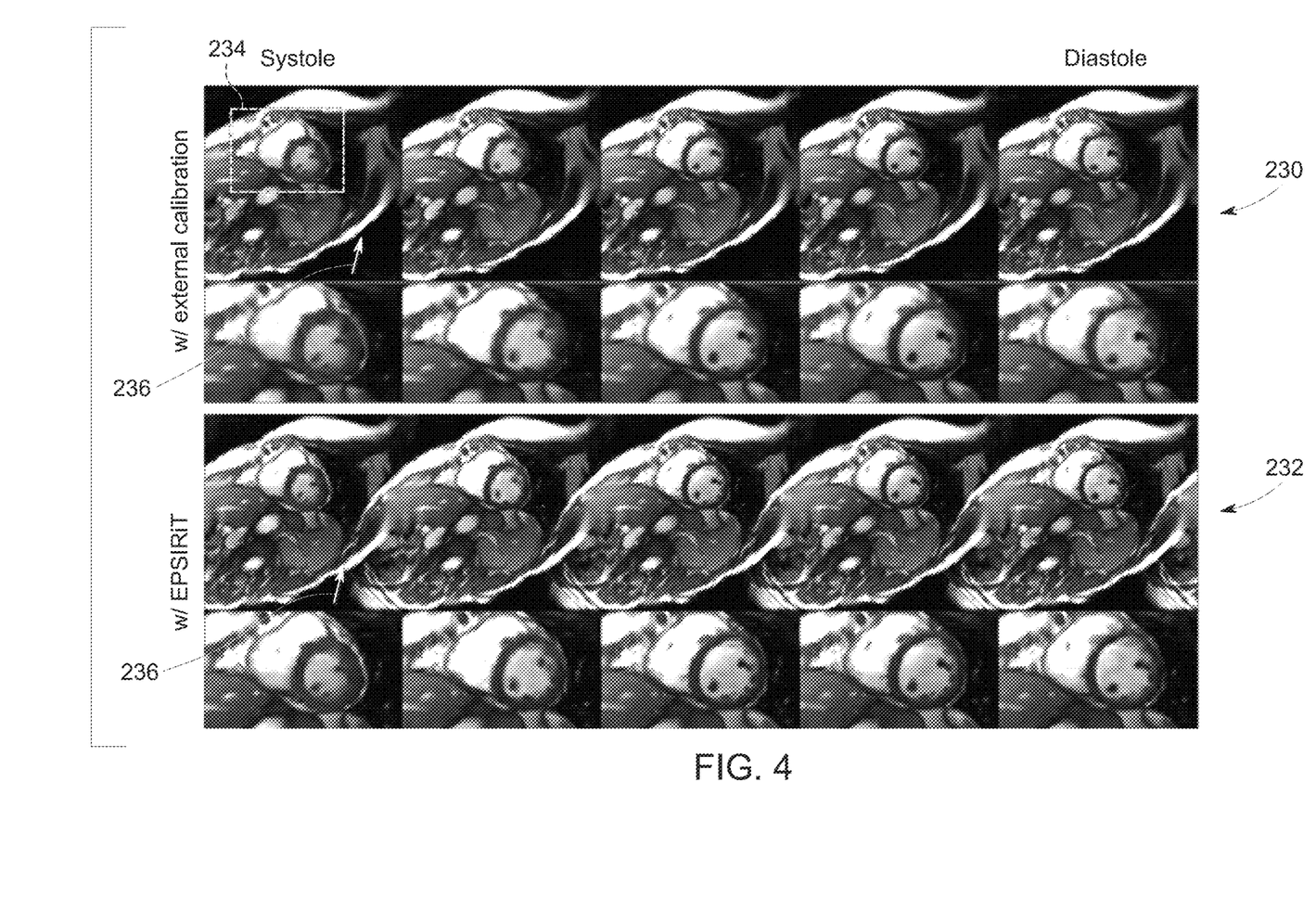
FIG. 4 illustrates a comparison of MR images reconstructed utilizing external calibration and MR images reconstructed utilizing self-calibration.

FIG. 4 illustrates a comparison of MR images reconstructed utilizing external calibration and MR images reconstructed utilizing self-calibration. A top row of MR images 230 of a heart were reconstructed utilizing the unrolled neural network-based reconstruction with external calibration described above. A bottom row of MR images 232 of the heart were reconstructed utilizing a deep learning-based neural network utilizing self-calibration (e.g., ESPIRiT calibration which derives coil sensitivity maps from data acquired with a smaller or truncated-FOV). Each row of MR images 230, 232 comprises corresponding zoomed-in images for a region 234 (e.g., in dashed outline) of the heart. A 1.5T scanner with a 30-channel abdominal coil array was utilized to perform the scan. The scan included two sequences, a 3D Cartesian gradient echo (GRE) based coil calibration sequence and a separate 2D accelerated Cine sequence. The 3D GRE sequence was utilized for coil calibration. The scan FOV for the 3D GRE sequence was 50 centimeters (cm). The spatial resolution for the 3D GRE sequence was 1.5 cm. The readout bandwidth for the 3D GRE sequence was 62.5 kilohertz (kHz). The 2D accelerated Cine sequence was a 2D Cartesian FIESTA sequence with 12-fold acceleration with variable density k-t sampling used to acquire short-axis Cine images. The scan FOV for the 2D accelerated Cine sequence was 36 cm. The spatial resolution for the 2D accelerated sequence was 1.4 millimeters. The readout bandwidth for the 2D accelerated sequence was 15 kHz. The images capture the cardiac cycle from the systole phase to the diastole phase. In the area indicated by arrow 236 in the bottom row of images 232, aliasing artifacts are present. In the same area indicated by arrow 236 in the top row of images 230, aliasing artifacts are not present. In addition, the quality of the images in both rows 230, 232 are the same. Thus, the reconstruction of images utilizing external calibration results in similar quality images (without the aliasing artifacts) compared to ESPIRiT based reconstruction.

Technical effects of the disclosed subject matter involve providing systems and methods for DL-based MRI reconstruction with extended FOV coil sensitivity calibration (e.g., external coil sensitivity calibration when derived from a separate scan). The improved DL-based accelerated MRI reconstruction utilizing extended FOV coil sensitivity calibration may minimize or eliminate aliasing artifacts (i.e., tissue wrapping effects) that typically occur with iterative DL reconstruction while maintaining image quality.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . ." or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A deep learning-based image reconstruction system, comprising:
a memory encoding processor-executable routines;
a processing component configured to access the memory and to execute the processor-executable routines, wherein the routines, when executed by the processing component, cause the processing component to:
provide sensitivity maps for coils of a magnetic resonance imaging (MRI) system to a neural network;
provide interleaved k-space data to the neural network, wherein the interleaved k-space data comprises partial k-space data interleaved with zeros, or synthesized k-space data, to provide an extended field of view (FOV) different from a FOV utilized during acquisition of the partial k-space data, wherein the partial k-space data were obtained during a scan of a region of interest with the MRI system; and output, from the neural network, at least one final reconstructed MR image based at least on the sensitivity maps and the interleaved k-space data, wherein the a least one final reconstructed MR image comprises the FOV utilized during the acquisition of the partial k-space data.

2. The image reconstruction system of claim 1, wherein outputting, utilizing the neural network, the at least one final reconstructed MR image comprises:

generating, via the neural network, at least one reconstructed MR image based at least on the sensitivity maps and the interleaved k-space data, wherein the at least one reconstructed MR image is at the extended FOV; and adjusting the at least one reconstructed MR image to the FOV utilized during the acquisition of the partial k-space data to generate the at least one final reconstructed MR image.

3. The image reconstruction system of claim 2, wherein adjusting the at least one reconstructed MR image to the FOV utilized during the acquisition of the partial k-space data comprises combining a multi-channel output for the at least one reconstructed MR image into a single channel output for the at least one final reconstructed MR image.

4. The image reconstruction system of claim 1, wherein the extended FOV is provided in the phase encoding dimension.

5. The image reconstruction system of claim 1, wherein the network comprises an unrolled neural network.

6. The image reconstruction system of claim 1, wherein the scan comprises an accelerated scan utilizing parallel imaging.

7. The image reconstruction system of claim 1, wherein the routines, when executed by the processing component, cause the processing component to extract the sensitivity maps from calibration data acquired during the scan or a separate external calibration scan based on both a location of the scan and the extended FOV, wherein the sensitivity maps comprise an extended calibration FOV.

8. The image reconstruction system of claim 7, wherein a FOV of the scan or the separate external calibration scan to acquire the calibration data is larger than the FOV utilized during acquisition of the partial k-space data.

9. The image reconstruction system of claim 8, wherein an area outside a central k-space region of the extended calibration FOV is filled with zeros for all channels.

10. A deep learning-based image reconstruction method, comprising:

providing, via a processor, sensitivity maps for coils of a magnetic resonance imaging (MRI) system to a neural network;

providing, via the processor, interleaved k-space data to the neural network, wherein the interleaved k-space data comprises partial k-space data interleaved with zeros, or synthesized k-space data, to provide an extended field of view (FOV) different from a FOV utilized during acquisition of the partial k-space data, wherein the partial k-space data were obtained during a scan of a region of interest with the MRI system; and outputting from the neural network, via the processor, at least one final reconstructed MR image based at least on the sensitivity maps and the interleaved k-space data, wherein the at least one final reconstructed MR image comprises the FOV utilized during the acquisition of the partial k-space data.

11. The image reconstruction method of claim 10, wherein outputting from the neural network, via the processor, the at least one final reconstructed MR image comprises:

generating, via the neural network, at least one reconstructed MR image based at least on the sensitivity maps and the interleaved k-space data, wherein the at least one reconstructed MR image is at the extended FOV; and adjusting, via the processor, the at least one reconstructed MR image to the FOV utilized during the acquisition of the partial k-space data to generate the at least one final reconstructed MR image.

12. The image reconstruction method of claim 11, wherein adjusting the at least one reconstructed MR image to the FOV utilized during the acquisition of the partial k-space data comprises combining a multi-channel output for the at least one reconstructed MR image into a single channel output for the at least one final reconstructed MR image.

13. The image reconstruction method of claim 10, wherein the extended FOV is provided in the phase encoding dimension.

14. The image reconstruction method of claim 10, wherein the network comprises an unrolled neural network.

15. The image reconstruction method of claim 10, wherein the separate scan comprises an accelerated scan utilizing parallel imaging.

16. The image reconstruction method of claim 10, comprising extracting, via the processor, the sensitivity maps from calibration data acquired during the scan or a separate external calibration scan based on both a location of the scan and the extended FOV, wherein the sensitivity maps comprise an extended calibration FOV.

17. The image reconstruction method of claim 16, wherein a FOV of the scan or the separate external calibration scan to acquire the calibration data is larger than the FOV utilized during acquisition of the partial k-space data.

18. The image reconstruction method of claim 17, wherein an area outside a central k-space region of the extended calibration FOV is filled with zeros for all channels.

19. A non-transitory computer-readable medium, the computer-readable medium comprising processor-executable code that when executed by a processor, causes the processor to:

provide sensitivity maps for coils of a magnetic resonance imaging (MRI) system to a neural network;

provide interleaved k-space data to the neural network, wherein the interleaved k-space data comprises partial k-space data interleaved with zeros, or synthesized k-space data, to provide an extended field of view (FOV) different from a FOV utilized during acquisition of the partial k-space data, wherein the partial k-space data were obtained during a scan of a region of interest with the MRI system; and output, from the neural network, at least one final reconstructed MR image based at least on the sensitivity maps and the interleaved k-space data, wherein the at least one final reconstructed MR image comprises the FOV utilized during the acquisition of the partial k-space data.

20. The non-transitory computer-readable medium of claim 19, wherein the scan comprises an accelerated scan utilizing parallel imaging.

* * * * *